United States Patent [19]

Bright et al.

[11] Patent Number: 5,565,453

[45] Date of Patent: Oct. 15, 1996

[54] NEUROLEPTIC 2-SUBSTITUTED PERHYDRO-1-H-PYRIDO[1,2-A]PYRAZINES

[75] Inventors: Gene M. Bright, Groton; Kishor A. Desai, Ledyard; Thomas F. Seeger, Mystic; Teresa A. Smolarek, Ledyard, all of Conn.

[73] Assignee: Pfizer Inc., New York, N.Y.

[21] Appl. No.: 211,054

[22] PCT Filed: Aug. 14, 1992

[86] PCT No.: PCT/US92/06625

§ 371 Date: Mar. 24, 1994

§ 102(e) Date: Mar. 24, 1994

[87] PCT Pub. No.: WO93/06101

PCT Pub. Date: Apr. 1, 1993

Related U.S. Application Data

[63] Continuation of Ser. No. 765,332, Sep. 25, 1991, abandoned.

[51] Int. Cl.[6] ...................... A61K 31/495; C07D 471/06
[52] U.S. Cl. ............................................ 514/249; 544/230
[58] Field of Search ............................... 544/230; 514/249

[56] References Cited

U.S. PATENT DOCUMENTS

| | | | |
|---|---|---|---|
| 4,831,031 | 5/1989 | Lowe, III et al. | 514/254 |
| 4,956,368 | 9/1990 | Cipollina et al. | 514/254 |
| 4,957,916 | 9/1990 | Kinnis et al. | 514/254 |

FOREIGN PATENT DOCUMENTS

| | | |
|---|---|---|
| 0196132 | 10/1986 | European Pat. Off. . |
| 0353821 | 2/1990 | European Pat. Off. . |
| 0380217 | 8/1990 | European Pat. Off. . |
| 9008144 | 8/1990 | WIPO . |

OTHER PUBLICATIONS

"Biochemical Profile of Risperidone, A New Antipsychotic", Leysen, J. E., et al., J. Pharm. Exp. Ther., 247, 661–670 at 662, 1988.

"The Oxford Textbook of Clinical Pharmacology and Drug Therapy", pp. 23–24, Grahame–Smith, D. G., et al. 1984.

Goodman and Gilman, "The Pharmacological Basis of Therapeutics", p. 13, 1990.

"Pharmacology of Risperidone (R 64 766), a New Antipsychotic with Serotonin–$S_2$ and Dopamine–$D_2$ Antagonistic Properties", Janssen, P. A. J., et al., Pharm. Exp. Ther., 244(2):685 1988.

"Risperidone in the Treatment of Acute Exacerbation of Chronic Schizophrenia", Borison, R. L. et al., Schizophrenia Research, 4(3):314–315, 1991.

"Therapeutic Effect and Safety of Increasing Doses of Risperidone (R 64766) in Psychotic Patients", Mesotten, et al., Psychopharmacology, 99:445–449, 1989.

*Primary Examiner*—Mark L. Berch
*Attorney, Agent, or Firm*—Peter C. Richardson; Paul H. Ginsburg; Garth Butterfield

[57] ABSTRACT

Antipsychotic compounds having the formula

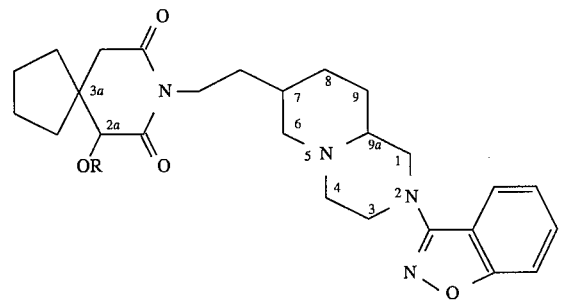

wherein R is hydrogen, acyl or substituted acyl; and a pharmaceutically acceptable acid addition salt thereof.

7 Claims, No Drawings

NEUROLEPTIC 2-SUBSTITUTED PERHYDRO-1-H-PYRIDO[1,2-A]PYRAZINES

CROSS REFERENCE TO RELATED APPLICATION

This application is the National Phase of International Application PCT/US92/06625, filed Aug. 18, 1992 and published as WO93/06101 Apr. 1, 1993 as a continuation of U.S. Ser. No. 07/765,332, filed Sep. 25, 1991 abandoned.

BACKGROUND OF THE INVENTION

The present invention is directed to certain 2- substituted perhydro-1H-pyrido[1,2-a]pyrazines which are depicted by the formula (I) as defined below, and to pharmaceutical compositions comprising these compounds, and a method of treating psychotic diseases therewith.

Commonly-owned U.S. patent application No. 07/661, 791, filed Feb. 27, 1991 U.S. Pat. No. 5,157,034, the disclosure of which is herein incorporated by reference, is directed to both racemic and optically active perhydro-1H-pyrido[1,2-a]pyrazines having the formula

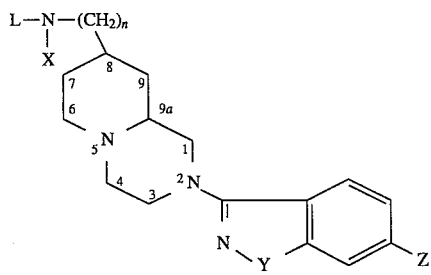

wherein
Z is H or Cl;
Y is O or S;
n is 1, 2, 3 or 4; and when
L and X are taken together are:

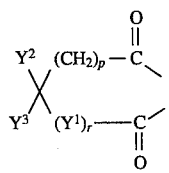

where $Y^1$ is $CH_2$, S, O or NH; $Y^2$ and $Y^3$ are taken separately and $Y^2$ and $Y^3$ are each independently hydrogen or methyl, or $Y^2$ and $Y^3$ are taken together and are $(CH_2)_q$; p is 1 or 2, q is 2, 3, 4 or 5; and r is 0 or 1.

U.S. Pat. No. 4,956,368, issued Sep. 11, 1990 discloses various metabolites and prodrug formulations of 8-[4-[4-(1, 2-benzisothiazol-3-yl)-1-piperazinyl]butyl]-8-azaspiro(4, 5)decane-7,9-dione which are particularly useful in the treatment of psychotic disorders, especially derivatives thereof which have been oxygenated at specified sites about the original structure, rearranged compounds, and prodrug formulations of these species. One particularly desired group of compounds have the general formula

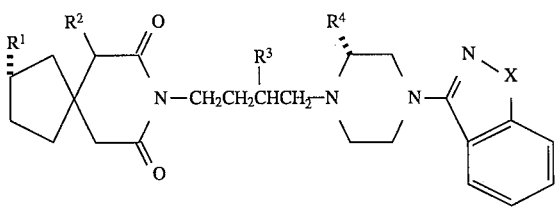

where:
$R^1$ is hydrogen, hydroxyl, alkoxy, acyloxy and oxo;
$R^2$ is hydrogen, methyl, hydroxyl, alkoxy and acyloxy;
$R^3$ is hydrogen, hydroxyl, and methoxy;
$R^4$ is hydrogen, methyl and oxo; and
X is S, SO, and $SO_2$.

Perhydro-1H-pyrido[1,2-a]-pyrazines of the formula

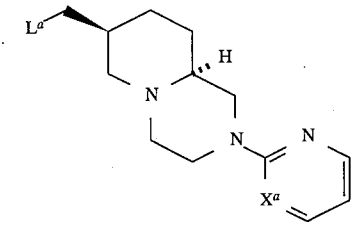

wherein $X^a$ is N or CH and $L^a$ represents one of certain pyrazolo, triazolo, tetrazolo or cyclic imido radicals have been reported to possess useful anxiolytic activity, Bright and Desai, International Application published under the PCT as publication No. WO 90/08144.

A variety of compounds are reported to be in possession of neuroleptic activity useful in the treatment of psychotic diseases. These include piperidine derivatives of the formula

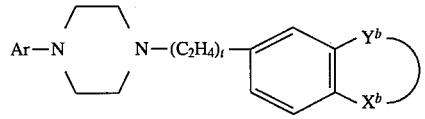

wherein t is 1 or 2, Ar is naphthyl or one of a variety of bicyclic heteroaryl groups, including benzisothiazoyl, and $X^b$ and $Y^b$ together with the attached phenyl group form a similar such bicyclic heteroaryl group (Lowe, III et al., U.S. Pat. No. 4,831,031); and compounds of the formula

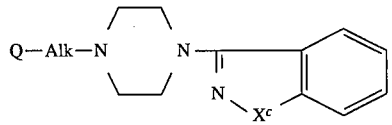

wherein Q represents certain bicyclic heteroaryl groups, Alk is alkanediyl $X^c$ represents, O, S, NH, or substituted NH (Kennis et al., U.S. Pat. No. 4,957,916).

SUMMARY OF THE INVENTION

The present invention is directed to 2-substituted perhydro-1H-pyrido-[1,2-a]pyrazines having the formula

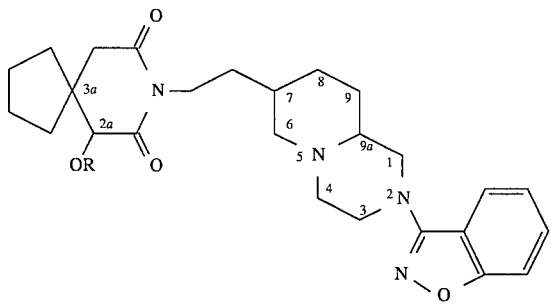

(I)

wherein R is H or $R^1C(=O)$, wherein $R^1$ is $(C_1-C_6)$alkyl, phenyl or substituted phenyl.

DETAILED DESCRIPTION OF THE INVENTION

The present invention is directed to 2a-oxo-substituted perhydro-1H-pyrido[1,2-a]pyrazines having the formula I wherein the stereochemistry at the 2a position is R or S; or a diastereomeric mixture which comprises the compound of formula (I) having 2aR, 7S, 9aS stereochemistry in combination with the compound of formula (I) having 2aS, 7S, 9aS stereochemistry; and a pharmaceutically acceptable acid addition salt thereof; and wherein R is hydrogen or $R^1C(=O)$ wherein $R^1$ is $(C_1-C_6)$-alkyl, phenyl or substituted phenyl.

As used in this invention "alkyl" means straight or branched carbon chains of up to six carbon atoms.

"Substituted phenyl" means a phenyl ring having one or two substitutions selected from $(C_1-C_6)$ alkyl, $(C_1-C_6)$ alkoxy, halo, nitro and trifluoromethyl.

In another aspect, this invention is directed toward a pharmaceutical composition for the treatment of psychotic disorders which comprises a neuroleptic effective amount of a compound of formula I and a pharmaceutically acceptable carrier.

In yet another aspect, this invention is directed toward a method of treating psychotic disorders which comprises administering to a psychotic patient in need of such treatment a neuroleptic effective amount of a compound of formula I.

A preferred compound of this invention is represented by formula I wherein R is H and wherein the compound has 2aR, 7S, 9aS stereochemistry or 2aS, 7S, 9aS stereochemistry or the above two compounds in combination.

The present invention is readily carded out. In a preferred process an amine of formula II

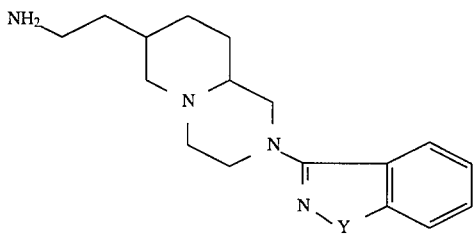

(II)

is heated with an excess of 3,3-tetramethylene glutaric anhydride to form the intermediate of formula III as described in U.S. patent application No. 07/661,791, filed Feb. 27, 1991 U.S. Pat. No. 5,157,034.

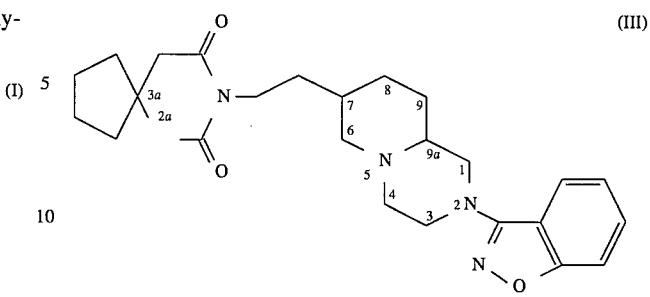

(III)

Alternatively, this cyclic imide may be prepared by reaction of substantially one equivalent of cyclic anhydride, generally under more moderate temperature conditions so as to form an intermediate half-amide half-acid which is then cyclized by heating with a more readily available anhydride such as acetic anhydride.

Detailed procedures for the preparation of compounds II and III and other intermediates are described in Preparations 1–12.

Compound I, R is H, may be prepared from compound III by oxidation of the corresponding alkali metal mono-enolate salt of the glutarimide moiety within compound III (formed by treatment of III with a sufficiently strong alkali metal anionic base such as sodium bis(trimethylsilyl)amide) with camphorsulfonyl oxaziridine in an inert solvent, followed by aqueous acidification of the reaction. This reaction is preferably carded out at a reduced temperature; temperatures of −60° C. to −78° C. were found to be suitable. The resulting product is isolated and purified by standard methods which are obvious to the chemist of ordinary skill.

Compound I, R is $R^1C(=O)$, may be conveniently prepared by reacting compound I, R is H, with the appropriate acid halide or acid anhydride, $R^1C(=O)x$ or $(R^1C(=O))_2O$, in which $R^1$ is selected from $C_1-C_6$ alkyl, phenyl or substituted phenyl, and X is chloro or bromo. This reaction may be conveniently carded out in an inert solvent with an acid acceptor. The conditions of this reaction are not critical and will be obvious to the chemist of ordinary skill.

All clinically effective antipsychotic agents block dopamine binding to D-2 receptors, and demonstrate functional antagonism of dopamine-mediated behaviors in animals. Although the standard antipsychotics interact with a wide variety of neuro transmitter receptors, their potency in blocking D-2 binding is the only activity which shows a highly significant correlation with their oral clinical dosage (Creese et al., Science, 192:481–483, 1976). This clinical effect is believed to result from actions on mesolimbic-mesocortical dopamine projections to the forebrain, specifically inhibition of dopamine hypersensitivity caused by increased receptor density, as demonstrated in postmortem studies of schizophrenic brains (Lee et al., Nature, 274:897, 1978).

The relative ability of the present compounds of the formula (I) to displace binding at the D-2 receptors was determined according to standard radioligand homogenate binding techniques, as follows. Adult, male Sprague-Dawley rats (3 per assay) were decapitated, the brains quickly removed and caudate-putamen was dissected out. Tissue was homogenized in 50 volumes of ice-cold 50 mM Tris-HCl buffer containing 100 mM NaCl and 1 mM $MgCl_2$ and adjusted to pH 7.2. This mixture was centrifuged twice at 20,000×g for 15 minutes each, the supernatant being discarded each time and the pellet resuspended in fresh buffer with homogenization. The final pellet was resuspended in buffer to a concentration of 5.6 mg/ml. This tissue suspension was then added to tubes containing a fixed concentration of 3H-spiroperiodol (0.2 nM), and various concentrations of test drug. Other tubes contained only buffer ("total") or a saturating concentration of (+)butaclamol (10 µM="blank"). The tubes (final volume—1.0 ml) were incubated at 37° C. for 15 minutes, then rapidly filtered under vacuum through glass fiber filters and rinsed with 12 ml of ice-cold buffer in a Brandel Cell Harvester; The filters were then removed and counted in a scintillation counter using 5 ml of Beckman Readysafe scintillation fluid. The resulting counts were then used to generate the $IC_{50}$, or extrapolated concentration of test drug necessary to inhibit one-half of the binding, for each compound in question. (Method of Leysen et ed., Biochemical Pharmacology, 27;307–316 (1978).

The antipsychotic activity of the present compounds is also demonstrated by their neuroleptic activity using methods based on standard procedures. In one method, adult male Sprague-Dawley rats are pretreated with appropriate doses of the test compound by subcutaneous injection. One half hour later, all rats are injected intraperitoneally with 1 mg/kg apomorphine hydrochloride dissolved in an 0.1% ascorbate solution. The rats are rated behaviorally according to the following stereotypy scale at 5, 15, 25, 35 and 45 minutes after the apomorphine injection: 0=alert but not moving, 1=moving about in the cage, 2=discontinuous sniffing behavior, 3=continuous sniffing with discontinuous oral movements. Compounds with neuroleptic activity will lower the overall stereotype score of the drug-treated groups, relative to untreated control rates, in proportion to their antagonist potency of the dopamine receptor.

The biological activity of the compounds of this invention makes them useful for treating psychotic disorders in human subjects. For example, these compounds are useful for treating psychotic disorders of the schizophrenic types, and in particular the compounds are useful for removing or ameliorating such symptoms as anxiety, agitation, excessive aggression, tension and social or emotional withdrawal in psychotic patients.

A compound of formula (I), or a pharmaceutically-acceptable salt thereof, is administered to a human subject either alone, or preferably, in combination with pharmaceutically-acceptable carriers or diluents, in a pharmaceutical composition, according to standard pharmaceutical practice. These compositions are administered orally or parenterally. Parenteral administration includes especially intravenous and intramuscular administration. Additionally, in a pharmaceutical composition comprising a compound of formula (I), or a pharmaceutically-acceptable salt thereof, the weight ratio of active ingredient to carrier will normally be in the rage from 1:6 to 2:1, and preferably 1:4 to 1:1. However, in any given case, the ratio chosen will depend on such factors as the solubility of the active component, the dosage contemplated and the precise route of administration.

For oral use of neuroleptic agent of this invention, the compounds are administered, for example, in the form of tablets or capsules, or as an aqueous solution or suspension. In the case of the tablets for oral use, carriers which can be used include lactose and cornstarch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When an agent of this invention is to be used in a human subject to treat a psychotic disorder, the daily dosage will normally be determined by the prescribing physician. Moreover, the dosage will vary according to the age, weight and response of the individual patient as well as the severity of the patient's symptoms. However, in most instances, an effective amount for treating a psychotic disorder will be a daily dosage in the range from about 1 to 500 mg. preferably about 5 to 100 mg, in single or divided doses, orally or parenterally. In some instances it may be necessary to use dosages outside these limits.

The following examples are provided solely for the purpose of further illustration. Nomenclature used herein, including designation of relative stereochemistry (R*, S*) and absolute stereochemistry (R, S), is according to Rigaudy et al., IUPAC Nomenclature of Organic Chemistry, 1979 Edition, Pergamon Press, New York.

EXAMPLE 1

(7S,9aS)-2-(benzo[d]isoxazol-3-yl)perhydro-7-(2-((2aS)-2a-hydroxy-3,3-tetramethyleneglutarimido)ethyl)-1H- pyrido[1,2-a]pyrazine and
(7S,9aS)-2-(benzo[d]isoxazol-3-yl)perhydro-7-(2-((2aR)-2a-hydroxy-3,3-tetramethyleneglutarimido)ethyl)-1H-pyrido-[1,2-a]-pyrazine (mixture of two diastereomers) Compound I, R=H To a stirred solution of optically active (7S,9aS)-2-(benzo [d]isoxazol-3-yl)perhydro- 7-(2-(3,3-tetramethylene-glutarimido)ethyl)-1H-pyrido[1,2-a]pyrazine, (Preparation 12, 563 mg, 1.25 mmol) in anhydrous tetrahydrofuran chilled to −78° C., 1.37 ml of a 1.0M solution of sodium bis(trimethylsilyl)amide (1.37 mmol) in anhydrous tetrahydrofuran (Aldrich Chemical Co.) was added all at once. After stirring for 15 minutes (−78° C.), (+)-(2R, 8aS)-(camphorsulfonyl)oxaziridine (Aldrich Chemical Co., 570 mg, 2.5 mmol) was added, and the reaction was stirred for 2.5 hours (temperature range −60° C. to −78° C.). After acidification by addition of saturated aqueous ammonium chloride (5 ml), the solvent was removed in vacuo. The residue was dissolved in well-stirred methylene chloride/aqueous sodium carbonate (pH=8.5) mixture (50 ml of each). The separated organic phase was dried (anhydrous sodium sulfate) and concentrated in vacuo to a solid. Silica gel flash chromatography of the entire sample (40 g silica gel, 32–63 mesh, eluting initially with methylene chloride/methanol=100:1.25 in volume, gradually increasing the polarity of the system to a final methylene chloride/methanol ration of 100:2.5 in volume) afforded 180 mg (31% yield) of the titled compound (mixture of two diastereomers) as a colorless amorphous solid. Thin Layer Chromatography (TLC) $R_f$ (methylene chloride/methanol=9:1 in volume):0.48. $^{13}$CNMR (CDCl$_3$) delta 25.5, 25.9, 29.3, 29.7, 30.4, 32.5, 34.1, 35.9, 38.3, 44.6, 44.8, 48.2, 53.7, 54.2, 60.2, 61.3, 74.3, 110.5, 116.2, 122.1, 122.2, 129.5, 161.1, 164.0, 170.8, 175.1;

MS m/z 468(M, $C_{26}H_{34}N_4O_4$).

The same product (diastereometric mixture) is obtained when (−)-(2S, 8aR)-(camphorsulfonyl)oxaziridine (Aldrich Chemical Co.) is utilized as the oxidant.

The presence of both diastereomers was confirmed by means of a Chiral HPLC diastereoselective assay.

PREPARATION 1 trans-5-(Methoxycarbonyl)piperidine-2-carboxylic Acid

Dimethyl cis-piperidine-2,5-dicarboxylate (20 g, 0.077 mol), salicylaldehyde (3 ml, about 0.014 mol) and acetic acid (200 ml) were combined and heated at reflux for 24 hours. The mixture was cooled and stripped in vacuo to a thick oil. The residue was taken up in 300 ml of isopropyl alcohol and restripped to 200 ml, by which time product began to precipitate. After granulating for 2 hours, title product was recovered by filtration and air dried, 9.20 g; m.p. 184° C. (softening), 191°–200° C. (dec.); ¹H-NMR(CDCl$_3$, 300 MHz)delta: 3.73 (s, 3H), 3.62 (septet, 2H(, 3.15 (t, 1H), 2.90 (m, 1H), 2.30 (m, 2H), 1.74 (m, 2H).

Crude cis-5-(methoxycarbonylpiperidine-2-carboxylic acid, containing some additional mount of the trans-isomer, 4.52 g, was recovered by stripping mother liquors. This material is suitable for recycling in the present process in place of dimethyl cis-piperidine-2,5-dicarboxylate.

Substitution of benzaldehyde for salicylaldehyde gave the same products, but the desired equilibrium mixture of cis and trans acids was achieved more slowly.

PREPARATION 2

3:1 Mixture of trans and cis-5-(Methoxycarbonyl)piperidine-2-carboxylic Acid Dimethyl cis-piperidine-2,5-dicarboxylate (112 g, 0.56 mol), salicylaldehyde (3 ml, 0.056 mol) and glacial acetic acid (600 ml) were combined and the resulting mixture heated at about 100° C. for 60 hours. The mixture was cooled, than stripped in vacuo to a thick oil from which 61.7 g (59%) of title products crystallized upon stirring with 800 ml of isopropyl alcohol. Product ratio was determined by ¹H-NMR (D$_2$O, 300 MHz), a peak at 3.13 pp, (t, 1 H, J=14.5 Hz) being diagnostic of trans, and a peak at 3.3 ppm (dd, 1H) being diagnostic of cis.

PREPARATION 3

Dimethyl trans-Piperidine-2,5- dicarboxylate Hydrochloride

Method A

Title product mixture of the preceding Preparation (15.1 g, 0.08 mol) was suspended in 200 ml of methanol and stirred under N$_2$ at 0°–5° C. Thionyl chloride (7.35 ml, 0.1 mol) was added dropwise over about 5 minutes. After 30 minutes the mixture was warmed to room temperature, and after 1 hour warmed to reflux for 6 hours. Upon cooling title product (6.8 g) crystallized from the reaction mixture. A second and third crop (5.3 g and 0.63 g) were obtained by stripping mother liquors to low volume and diluting to 200 ml with isopropyl alcohol. The combined yield of present title product was 67%; m.p. 207°–209° C. Analysis calculated: C, 45.48; H, 6.79; N, 5.89. Found: C, 45.34; H, 6.55; N, 5.82.

Dimethyl cis-piperidine-2,5-dicarboxylate recoverable from mother liquors is recycled as starting material in Preparation 1 or 2 above.

Method B

In like manner, title product of Preparation 1 is converted to present title product.

PREPARATION 4

Racemic Dimethyl trans-1-(2-Phthalimido)ethyl)piperidine-2,5-dicarboxylate

To a well-stirred bi-phasic mixture consisting of sodium carbonate (500 g, 4.72 mol) in water (3 liters) and trans-2,5-piperidine dicarboxylate dimethyl ester hydrochloride (280 g, 1.18 mol) in methylene chloride (4.5 liters), a solution of 2-phthalimido-ethyl triflate (417 g, 1.29 mol)in methylene chloride (3 liters) was added in a steady stream over a 3 hour period. The organic layer was separated, and the aqueous layer was extracted with fresh methylene chloride (3 liters). The combined organic extracts were washed with water (3 liters), then with brine (3 liters), dried with anhydrous magnesium sulfate and finally, concentrated in vacuo to solid. The entire residue was triturated in refluxing ether (3 liters), with vigorous stirring, for 15 minutes. After cooling to ambient temperature, the solution was poured into hexanes (3 liters), and the resulting mixture was stirred for 18 hours. The resulting colorless solid was collected by filtration, and the filter cake was washed with hexanes (1 liter). In vacuo drying afforded 437.3 g (99.1% yield) of the titled compound as a colorless solid. TLC Rf (ethyl acetate/methylene chloride=1:1 in volume; iodoplatinate spray): 0.5.

PREPARATION 5

RacemicMethyl(7R*,9aS*)-4,6,7,8,9,9a-Hexahydro-2H,3H-pyrido[1,2-a]-pyrazine-1-one- 7-carboxylate To a well-stirred suspension of the title product of Preparation 4 (194 g, 0.52 mol) in methanol (3 liters), hydrazine monohydrate (57.1 g, 1.14 mol) was added. The reaction mixture was then stirred for 18 hours at ambient temperature. Methylene chloride (2 liters) was added, and the resulting mixture was vigorously stirred for 1 hour. The resulting white solids were filtered, and the filtercake was washed with methylene chloride (1 liter) before being discarded. In vacuo concentration of the filtrate afforded a colorless solid, which was granulated and then vigorously stirred in refluxing methylene chloride (3 liters) for 10 minutes. The cooled mixture was filtered, and the resulting filtrate was concentrated in vacuo to afford present title compound (89.4 g, 81.6% yield) as an ivory solid. TLC Rf (methylene chloride/methanol=9:1 in volume; iodoplatinate spray): 0.38.

PREPARATION 6

Racemic (7R*,9aS*)-Perhydro-7-(hydroxymethyl)-1H-pyrido[1,2-a]pyrazine

To a stirred slurry of the amide-ester title product of Preparation 5 (244 g, 1.15 mol) in anhydrous tetrahydrofuran (THF, 5.5 liters, a 1.0M solution of lithium aluminum hydride (2.33 liters, 2.33 mol) was added dropwise under nitrogen while maintaining the temperature of the reaction mixture below 40° C. The mixture was then heated at reflux for 18 hours. After cautious dropwise addition of water (90 ml) to the reaction (cooled to ambient temperature) followed by the addition of 15% aqueous sodium hydroxide (90 ml) and finally, more water (270 ml), the mixture was stirred for 1 hour. Insoluble inorganic salts were removed by filtration, and the resulting filtrate was concentrated in vacuo to afford present title compound as a light yellow solid (179.4 g, 90.6% yield), sufficiently pure for use in the next step without further purification. TLC Rf (methylene chloride/methanol/concentrated aqueous ammonia=3:1:0.1 in volume; iodoplatinate spray): 0.19.

PREPARATION 7

Racemic
(7R*,9aS*)-2-(Benzo[d]isoxazol-3-yl)-perhydro-
7-(hydroxymethyl)- 1H-pyrido[1,2-a]pyrazine A stirred solution of alcohol-amine title product of Preparation 6 (179.4 g, 1.05 mol), 3-chloro-1,2-benzo[d]-isoxazole (194.2 g, 1..26 mol), and 1,8-diazabicyclo-[5.4.0] undec-7-ene (DBU, 197.9 g, 1..30 mol) in pyridine (400 ml) was heated at 100° C. for 18 hours. After cooling to 35° C., water (3 liters), methylene chloride (2.5 liters) and, finally, saturated aqueous sodium carbonate (2 liters) were added, and the resulting biphasic mixture was vigorously stirred for 3 hours. The tan solid precipitate which formed during the stirring period was filtered, and the filter cake was washed first with water and then with hexane (1 liter of each) prior to being dried in vacuo. Trituration of the entire sample (216 g) with isopropyl alcohol (630 ml) followed by filtration and in vacuo drying afforded present title compound (154.5 g, 51% yield) as a light tan powder, sufficiently pure for use in the next step without further purification. TLC Rf (methylene chloride/methanol=9.1 in volume; idoplatinate spray): 0.50. $^{13}$CNMR (CDCl$_3$) delta 154.0, 161.1, 129.5, 122.3, 122.1, 116.2, 110.5, 66.3, 50.3, 58.7, 54.3, 53.7, 48.3, 39.1, 29.0, 26.7.

PREPARATION 8

Racemic
(7R*,9aS*)-2-(Benzo[d]isoxazol-3-yl)-perhydro-
7-(methanesulfonyloxymethyl)-1H-pyrido
[1.2-a]pyrazine To a chilled (5° C.) and stirred slurry of the alcohol title product of Preparation 7 (154.0 g, 0.54 mol) and triethylamine (81.76 ml, 59.6 g, 0.589 mol) in methylene chloride (3.0 liters) a solution of methanesulfonyl chloride (43.55 ml, 54.5 g, 0.563 mol) in methylene chloride (350 ml) was added dropwise over 30 minutes. TLC monitoring (methylene chloride/methanol=9:1 in volume; iodoplatinate spray) of the reaction mixture after an additional ½ hour of stirring Indicated incomplete reaction. Complete reaction was realized within ½ hour after addition of a second portion of triethylamine (8.23 ml, 6.0 g, 59.3 remol) and methanesulfonyl chloride [4.32 ml, 6.4 g, 55.9 mmol) added dropwise as a methylene chloride (20 ml) solution]. Water (3 liters) and methylene chloride (1.5 liters) were added, and the biphasic mixture was vigorously stirred prior to separation of the organic and aqueous phases. The aqueous portion was then extracted with a fresh portion of methylene chloride (1.5 liters). The organic extracts were then combined, washed with brine (twice with 2 liter portions) and dried over anhydrous sodium sulfate. Concentration in vacuo afforded the present title compound as a tan solid (178.0 g, 90.2% yield). TLC Rf (methylene chloride/methanol=9.1 in volume; iodoplatinate spray): 0.24. MS m/z 365.1 (M, C$_{17}$H$_{23}$N$_3$O$_4$S). $^{13}$CNMR (CDCl$_3$) delta 164.0, 160.9, 129.6, 122.4, 122.1, 116.0, 110.5, 71.9, 59.9, 57.7, 54.0, 53.3, 48.1, 37.4, 35.9, 28.4, 26.2.

PREPARATION 9

Racemic(7S*
,9aS*)-2-(Benzo[d]isoxazol-3-yl)-7-(cyanomethyl)
perhydro-1H-pyrido[1,2-a]pyrazine A stirred solution of the mesylate title product of Preparation 8 (177.5 g, 0.486 mol) and sodium cyanide (35.7 g, 0.729 mol) in N,N-dimethylformamide (3.0 liters) was heated at 110° C. for 18 hours. The solvent was removed in vacuo, and the resulting tan solid residue was dissolved in a water/methylene chloride (2.5 liters of each) biphasic mixture. The pH of the well-stirred mixture was adjusted to 10 (saturated aqueous sodium carbonate). The layers were then separated, and the aqueous phase was extracted with a fresh portion of methylene chloride (1.5 liters). The combined organic extracts were washed with brine (two 1 liter portions), dried over anhydrous sodium sulfate and concentrated in vacuo to afford present title compound as a tan solid (137.3 g, 95.3% yield). TLC Rf (ethyl acetate/hexane=1:1 in volume; iodoplatinate spray): 0.20. $^{13}$CNMR (CDCl$_3$)delta 164.0, 161.0, 129.6, 122.4, 122.0, 117.9, 116.0, 110.5, 59.9, 59.5, 53.9, 53.3, 48.1, 32.9, 29.6, 28.7, 22.1. In this product, the 7,9a-hydrogens are still trans.

PREPARATION 10

Racemic(7S*
,9aS*)-7-(2-Aminoethyl)-2-(benzo[d]isoxazol-3-yl)
perhydro-1H-pyrido[1,2-a]pyrazine To a stirred mixture of the nitrile title product of Preparation 9 (136.9 g, 0.462 mol) in anhydrous tetrahydrofuran (3.5 liters), a 1.0M solution of lithium aluminum hydride (LAH) in tetrahydrofuran (693 ml, 0.693 mol) was added dropwise over a 1 hour period. The reaction was heated at reflux for 6 hours, then stirred for 18 hours at ambient temperature and, finally, quenched by cautious dropwise addition of water/tetrahydrofuran (26 ml and 30 ml respectively), 15 percent aqueous sodium hydroxide (26 ml), and water (80 ml). The mixture was stirred for 0.5 hour. Anhydrous sodium sulfate (400 g) was added, and the inorganic salts were filtered. The filter cake was washed with tetrahydrofuran (800 ml) and methylene chloride (1 liter). The washings were combined, with the filtrate, and the resulting solution was concentrated in vacuo to afford the present title compound as a yellow solid (131.9 g, 95% yield). TLC Rf (methylene chloride/methanol/concentrated aqueous ammonia=9:1:0.1 in volume; iodoplatinate spray) 0.28. $^{13}$CNMR (CDCl$_3$) delta 164.0, 161.1, 129.4, 122.2, 122.1, 116.2, 110.4, 61.7, 60.2, 54.2, 53.8, 48.3, 39.7, 38.7, 33.9, 30.7, 29.4.

PREPARATION 11

Optically Active
(7S,9aS)-7-(2-Amino-ethyl)-2-(benzo[d]isoxazol-3-yl)
perhydro-1H-pyrido[1,2-a]pyrazine Racemic title amine of Preparation 10 (131.5 g, 0.438 mol) was dissolved in refluxing ethanol (2.4 liters). S-(+)-mandelic acid (66.6 g, 0.438 mol) was added, affording a clear solution which was allowed to cool slowly and stand at ambient temperature for 18 hours. The colorless crystalline precipitate was filtered, and the cake was washed thrice with 300 ml portions of diethyl ether. In vacuo drying afforded 92.6 g of colorless crystalline (partially resolved) salt; m.p. 205°–210° C. The entire sample was then refluxed in ethanol (1.8 liters) for one hour, affording a solution-suspension which was filtered after being allowed to cool to ambient temperature. Washing of the filter cake with two 300 ml portions of diethyl ether followed by drying in vacuo afforded 75.6 g of colorless crystalline, salt; m.p. 214°–217° C., further progresses toward optical resolution and isolation of the (7S,9aS)-(−)-enantiomer as its S-(+)-mandelic acid salt. Again, the entire sample was refluxed in ethanol (1.0 liter) for 0.5 hours, cooled to ambient temperature and allowed to stand for 18 hours. Filtration followed by diethyl ether-washing of the filter cake and in vacuo drying afforded 66.3 g of colorless crystals; m.p. 216°–218° C. The justdescribed crystallization procedure, utilizing 1 liter of ethanol as the crystallization solvent was repeated five more times to afford 45.1 g of resolved S-(+)mandelic acid salt of the (7S,9aS)-(−)-enantiomer; m.p. 223°–224 ° C. The entire sample was dissolved in a biphasic methylene chloride (2.5 liters)/water (1.4 liters) mixture with the pH adjusted to 9 (saturated aqueous sodium carbonate). The layers were separated, and the aqueous portion was extracted with 2 liters of fresh methylene chloride. Concentration in vacuo of the anhydrous sodium sulfate dried combined organic extracts afforded present title compound having 7,9a-hydrogen substituents trans (29.9 g, 45.4% yield) as a colorless amorphous solid. $[\alpha]_D$ −8.65° C. (c=3.73, methylene chloride). $^{13}$CNMR (CDCl$_3$) delta; identical to that of the racemic amine.

Optical resolution of the racemic (±)-amine to the present 7S,9aS-(−)-amine was confirmed by $^{19}$FNMR comparative studies of its chiral Mosher amide derivative with the corresponding derivative of its 7R,9aR-(+)-counterpart. Single crystal X-ray diffraction studies of the latter Mosher amide derivative established the absolute stereochemistry of the present title product.

PREPARATION 12

Optically Active
(7S,9aS)-2-(Benzo[d]isoxazol-3-yl)perhydro-7-(2-(3,3-tetramethyleneglutar-imido)ethyl)-1H-pyrido[1,2-a]pyrazine A mixture consisting of 7$\underline{S}$,9a$\underline{S}$-(−)-amine title product of Preparation 11 (1.53 g, 5.09 mmol) and 3,3-tetramethylene glutaric anhydride (0.94 g, 5.59 mmol, Aldrich Chemical Co.) in xylenes (60 ml, boiling range 139°–144° C.) was stirred and heated at 150° C. for 15 minutes. The xylenes were carefully removed in vacuo (considerable frothing occurs) to afford the crude non-cyclized acid-amide as an amber solid [TLC Rf (methylene chloride/methanol=9.1 in volume); iodoplatinate spray); 0.45] sufficiently pure for imide formation without purification. The entire sample was stirred and heated in acetic anhydride (42ml) at 100°–110° C. for 2.5 hours. The reaction mixture was concentrated in vacuo to afford a solid residue which was partitioned in a well-stirred methylene chloride/water (60 ml and 50 ml, respectively) mixture with the pH adjusted to 9.5 (saturated aqueous sodium carbonate). The phases were separated, and the aqueous phase was extracted with an equal volume of fresh methylene chloride. Concentration in vacuo of the combined organic extracts afforded a yellow solid. Flash chromatography of the entire sample (30 g silica gel, 32–63 mesh; eluting initially with methylene chloride and then adding methanol to increase the polarity of the eluting system to a final methylene chloride/methanol ratio of 97:3 in volume) afforded the pure (TLC inspection in a variety of eluting systems; potassium permanganate spray) title compound as a colorless amorphous solid (1.40 g, 61% yield). $[\alpha]^{20}_D$ −4.6° (c=2.3, methylene chloride). TLC Rf (ethyl acetate; potassium permanganate spray): 0.25. HRMS m/z 450.2639 (m, C$_{26}$H$_{34}$O$_3$N$_4$) $^{13}$CNMR (CDCl$_3$) delta 172.1, 164.0, 161.1, 129.5, 122.2, (2), 116.2, 110.5, 61.3, 60.2, 54.2, 53.8, 48.2, 44.9, 39.5, 37.5, 37.4, 34.2, 32.6, 30.4, 29.3, 24.2.

A 230 mg sample of the amorphous product was twice crystallized from isopropanol (2 ml portions), affording 150 mg (65.2% yield) of colorless crystals; m.p. 157°–158° C. The spectroscopic properties and optical rotation of the amorphous and crystalline materials were identical. An enantioselective, quantitative, High Performance Liquid Chromatography (HPLC) assay was developed using a Chiral Type AGP ($\alpha_1$-glycoprotein) column (mobile phase: 0.01M aqueous dihydrogen potassium phosphate/acetonitrile/dimethyloctylamine=900:100:0.2; flow rate: 0.9 ml/minute; ultraviolet HPLC detector at 215 nm wavelength). By this assay, the optical purity of title compound product was found to be ≧95%.

We claim:

1. A compound, of formula (I),

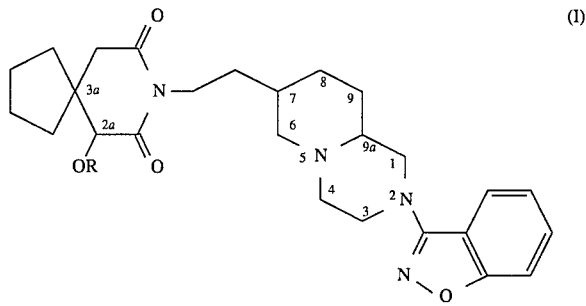

wherein R is hydrogen or R$^1$C(═O), wherein R$^1$ is (C$_1$–C$_6$)alkyl, phenyl, or phenyl substituted with one or two substituents selected from (C$_1$–C$_6$)alkyl, (C$_1$–C$_6$)alkoxy, halo, nitro and trifluoromethyl;

wherein the stereochemistry at the 2a position is R or S;

and a pharmaceutically acceptable acid addition salt thereof.

2. A diastereomeric mixture which comprises the compound of claim 1, wherein R is hydrogen, having 2aR, 7S, 9aS stereochemistry, and the compound of claim 1, wherein R is hydrogen, having 2aS, 7S, 9aS stereochemistry.

3. The compound of claim 1 wherein R is hydrogen having 2aR, 7S, 9aS stereochemistry, said compound being substantially free of any of its diastereomers.

4. The compound of claim 1 wherein R is hydrogen having 2aS, 7S, 9aS stereochemistry, said compound being substantially free of any of its diastereomers.

5. A pharmaceutical composition for the treatment of psychotic disorders in a human subject which comprises a neuroleptic effective mount of a compound of claim 1 and a pharmaceutically acceptable carrier.

6. A method of treating psychotic disorders which comprises administering to a psychotic patient in need of such treatment a neuroleptic effective mount of a compound of claim 1.

7. A process for preparing (7S,9aS)-2-(benzo[d]isoxazol-3-yl)perhydro-7-(2-((2aS)-2a-hydroxy-3,3-tetramethyleneglutarimido)ethyl)-1H-pyrido[1,2-a]pyrazine and (7S,9aS)-2-(benzo[d]isoxazol-3-yl)perhydro-7-(2-((2aR)-2a-hydroxy- 3,3-tetramethyleneglutarimido)ethyl)- 1H-pyrido[1,2-a]-pyrazine which comprises:

reacting (7S,9aS)-2-(benzo[d]isoxazol-3-yl)perhydro-7-(2-( 3,3-tetramethyleneglutarimido)ethyl)- 1H-pyrido[1,2-a]pyrazine, with sodium bis(trimethylsilyl)amide in a reaction inert solvent followed by reaction with (+)-(2R,8aS)-(camphorsulfonyl)oxaziridine; and acidifying and isolating said (7S,9aS)-2-(benzo[d]isoxazol-3-yl)perhydro-7-(2-((2aS)-2a-hydroxy-3,3-tetramethyleneglutarimido)ethyl)- 1H-pyrido[1,2-a]pyrazine and (7S,9aS)-2-(benzo[d]isoxazol-3-yl)perhydro- 7-(2-((2aR)-2a-hydroxy-3,3-tetramethyleneglutarimido)ethyl)-1H-pyrido[1,2-a]-pyrazine.

* * * * *